US011627968B2

(12) United States Patent
Baker (10) Patent No.: US 11,627,968 B2
(45) Date of Patent: Apr. 18, 2023

(54) INVAGINATOR FOR GASTROESOPHAGEAL FLAP VALVE RESTORATION DEVICE

(71) Applicant: EndoGastric Solutions, Inc., Redmond, WA (US)

(72) Inventor: Steve G. Baker, Redmond, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 513 days.

(21) Appl. No.: 16/923,085

(22) Filed: Jul. 8, 2020

(65) Prior Publication Data
US 2020/0330100 A1 Oct. 22, 2020

Related U.S. Application Data (60) Division of application No. 15/611,012, filed on Jun. 1, 2017, now Pat. No. 10,716,569, which is a division of application No. 13/710,419, filed on Dec. 10, 2012, now Pat. No. 9,675,360, which is a continuation of application No. 12/799,477, filed on Apr. 26, 2010, now abandoned, which is a continuation of application No. 12/383,836, filed on Mar. 26, 2009, now abandoned, which is a continuation of application No. 11/254,062, filed on Oct. 18, 2005, now abandoned.

(51) Int. Cl.
| | |
|---|---|
| *A61B 17/12* | (2006.01) |
| *A61B 17/068* | (2006.01) |
| *A61B 17/00* | (2006.01) |
| *A61B 17/30* | (2006.01) |
| *A61B 17/34* | (2006.01) |

(52) U.S. Cl.
CPC ............ *A61B 17/12* (2013.01); *A61B 17/068* (2013.01); *A61B 2017/00292* (2013.01); *A61B 2017/00827* (2013.01); *A61B 2017/306* (2013.01); *A61B 2017/3419* (2013.01); *A61B 2017/3488* (2013.01)

(58) Field of Classification Search
CPC .................. A61B 17/12; A61B 17/068; A61B 2017/00292; A61B 2017/00827; A61B 2017/306; A61B 2017/3419; A61B 2017/3488
See application file for complete search history.

(56) References Cited

U.S. PATENT DOCUMENTS

| | | | | |
|---|---|---|---|---|
| 2003/0216754 A1* | 11/2003 | Kraemer | ............ | A61B 17/0644 606/142 |
| 2006/0190018 A1* | 8/2006 | Baker | .................... | A61B 17/08 606/153 |
| 2007/0038232 A1* | 2/2007 | Kraemer | ............ | A61B 17/0644 606/153 |

* cited by examiner

*Primary Examiner* — Katherine M Rodjom
(74) *Attorney, Agent, or Firm* — Fulwider Patton LLP (57) ABSTRACT

An assembly for restoring a gastroesophageal flap valve includes a restoration device substantially free for rotation. The assembly comprises an elongated member configured to be fed through a throat, down an adjoining esophagus and into an associated stomach. The elongated member has a distal end. The assembly further comprises a gastroesophageal flap valve restoration device carried on the distal end of the elongated member for placement in the stomach, and an invaginator carried by the elongated member. The invaginator is configured to grip the esophagus and the elongated member and invaginator are coupled for restricted relative axial movement and substantially free relative rotational movement.

6 Claims, 4 Drawing Sheets

INVAGINATOR FOR GASTROESOPHAGEAL FLAP VALVE RESTORATION DEVICE

This application is a division of U.S. Ser. No. 15/611,012, filed Jun. 1, 2017, which is a division of U.S. Ser. No. 13/710,419, filed Dec. 10, 2012, now U.S. Pat. No. 9,675,360, issued Jun. 13, 2017, which is a continuation of U.S. Ser. No. 12/799,477, filed Apr. 26, 2010, now abandoned, which is a continuation of U.S. Ser. No. 12/383,836, filed Mar. 26, 2009, now abandoned, which is a continuation of U.S. Ser. No. 11/254,062, filed Oct. 18, 2005, now abandoned.

FIELD OF THE INVENTION

The present invention generally relates to a gastroesophageal flap valve restoration device for treating gastroesophageal reflux disease. The present invention more particularly relates to an invaginator for use in such devices that grips the esophagus during treatment and restricts axial device movement while permitting relatively free rotational device movement.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal flap to close and seal against high pressure in the stomach. Due to reasons including lifestyle, a Grade I normal gastroesophageal flap may deteriorate into a malfunctioning Grade III or absent valve Grade IV gastroesophageal flap. With a deteriorated gastroesophageal flap, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury. GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laparoscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable flap without a fixed portion. Hence, Nissen does not restore the normal movable flap. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180-degree valve is created by a system of sutures. The Hill procedure restores the moveable flap, the cardiac notch and the Angle of His. However, all of these surgical procedures are very invasive, regardless of whether done as a laparoscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak, in part due to the fact, that the esophagus is not covered by serosa, a layer of very sturdy, yet very thin tissue, covering and stabilizing all intraabdominal organs, similar like a fascia covering and stabilizing muscle. Involvement of esophageal tissue in the repair of a gastroesophageal flap valve poses unnecessary risks to the patient, such as an increased risk of fistulas between the esophagus and the stomach.

A new and improved apparatus and method for restoration of a gastroesophageal flap valve is fully disclosed in U.S. Pat. No. 6,790,214, issued Sep. 14, 2004, is assigned to the assignee of this invention, and is incorporated herein by reference. That apparatus and method provides a transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

Whenever tissue is to be maintained in a shape as, for example, in the improved assembly last mentioned above, it is necessary to first grip stomach tissue and then fasten at least two layers of gripped tissue together. In applications such as gastroesophageal flap valve restoration, it is desirable to grip stomach tissue displaced from the esophageal opening into the stomach so that when the stomach tissue is pulled aborally to form a flap, the flap will have sufficient length to cover the opening and function as a flap valve. With the gastroesophageal anatomy thus restored, the GERD will be effectively treated.

Locating the proper gripping point in the stomach is not a simple matter. Once a desired gripping point is found, it is then necessary to form the GEFV flap and maintain its shape without involving the esophageal tissue. Still further, these manipulations of the stomach tissue must be incrementally repeated many times as the device is rotated to form a complete valve. Such further manipulation must repeat the dimensions of the manipulated stomach tissue to result in a valve structure of uniform geometry. This requires the device to be disposed in a repeatable axial position for each manipulation. Unfortunately, this is extremely difficult under the circumstances provided by the anatomy of the stomach.

Hence, there is a need in the art for techniques and devices, which enable repeatable uniform manipulations of stomach tissue from within the stomach to restore a GEFV. The present invention addresses these and other issues.

SUMMARY

The invention provides an assembly comprising a medical instrument including an elongated member configured to be fed into a body space having sidewalls and an invaginator carried by the elongated member, the invaginator being configured to grip the body space sidewalls. The elongated member and invaginator are coupled for restricted relative axial movement and substantially free relative rotational movement.

The invention further provides an assembly comprising an elongated member configured to be fed through a throat, down an adjoining esophagus and into an associated stomach. The elongated member has a distal end. The assembly further includes a gastroesophageal flap valve restoration device carried on the distal end of the elongated member for placement in the stomach and an invaginator carried by the elongated member. The invaginator is configured to grip the esophagus and the elongated member and invaginator are coupled for restricted relative axial movement and substantially free relative rotational movement.

The invaginator may be configured to non-invasively grip the esophagus. To this end, the invaginator may be configured to vacuum-grip the esophagus.

The assembly may further comprise a conduit that couples the invaginator to a vacuum source. The conduit may comprise a lumen formed in the elongated member. Alternatively, the conduit may comprise an elongated tubular member independent of the elongated member.

The invaginator preferably circumscribes the elongated member. The assembly may further comprise a bearing assembly between the invaginator and the elongated member.

The bearing assembly may comprise at least one bearing sleeve. The bearing assembly may comprise an inner bearing sleeve and an outer bearing sleeve. The inner bearing sleeve and outer bearing sleeve are preferably coaxially disposed between the invaginator and the elongated member. A lubricant may be applied to the bearing assembly.

The elongated member may include a discrete axial length portion of reduced cross-sectional dimension and the invaginator may be confined within the discrete axial length portion to restrict its axial movement. Alternatively, the invaginator may extend substantially coextensively along the elongated member.

The invention further provides an assembly comprising an elongated member configured to be fed through a throat, down an adjoining esophagus and into an associated stomach, the elongated member having a distal end, a gastroesophageal flap valve restoration device carried on the distal end of the elongated member for placement in the stomach, and an invaginator carried by and circumscribing the elongated member. The invaginator is configured to vacuum grip the esophagus and the elongated member and invaginator are coupled for restricted relative axial movement and substantially free relative rotational movement.

The invention further provides an assembly comprising an elongated member having a distal end and configured to be fed through a throat, down an adjoining esophagus and into an associated stomach, a gastroesophageal flap valve restoration device carried on the distal end of the elongated member for placement in the stomach, an invaginator carried by and circumscribing the elongated member, the invaginator being configured to vacuum grip the esophagus, and a bearing assembly between the invaginator and the elongated member. The bearing assembly couples the elongated member and invaginator for restricted relative axial movement and substantially free relative rotational movement.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify like elements, and wherein:

DETAILED DESCRIPTION

Figure 1:
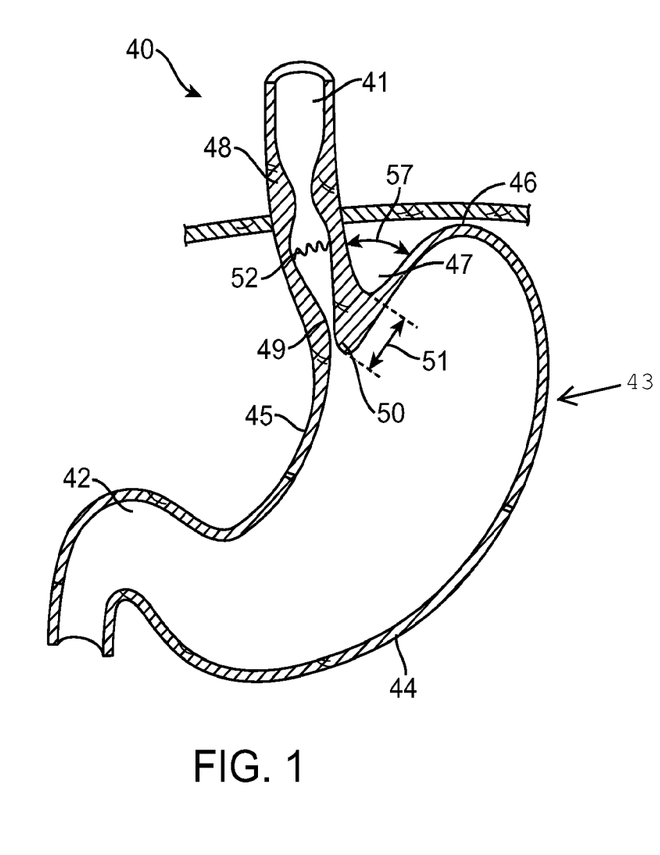
FIG. 1 is a front cross-sectional view of the esophageal-gastro-intestinal tract from a lower portion of the esophagus to the duodenum.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue.

The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion.

The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43. It is about 4 to 5 cm long (51) at it longest portion, and its length may taper at its anterior and posterior ends.

The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

Figure 2:
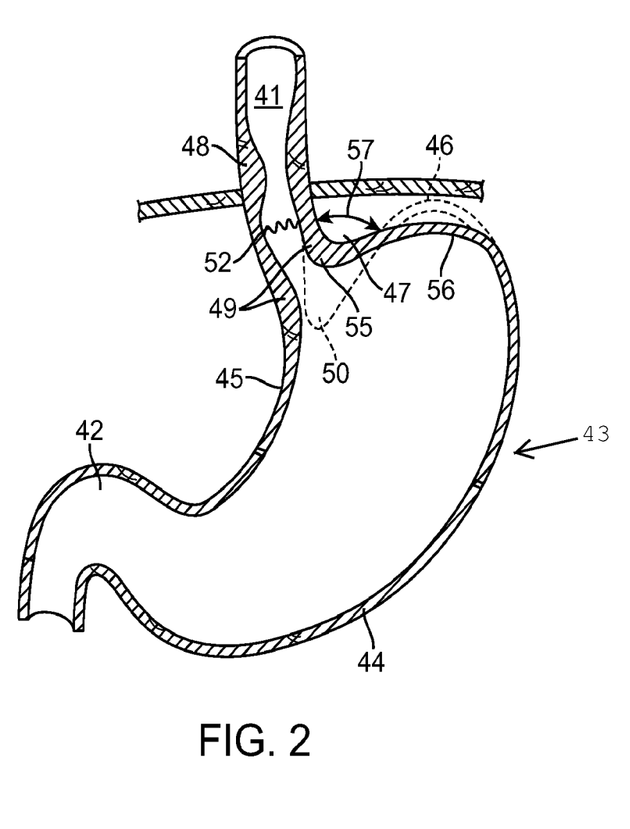
FIG. 2 is a front cross-sectional view of the esophageal-gastro-intestinal tract illustrating a Grade I normal appearance movable flap of the gastroesophageal flap valve (in dashed lines) and a Grade III reflux appearance gastroesophageal flap of the gastroesophageal flap valve (in solid lines)

FIG. 2 is a front cross-sectional view of an esophageal-gastro-intestinal tract illustrating a Grade I normal appearance movable flap 50 of the GEFV 49 (shown in dashed lines) and a deteriorated Grade III gastroesophageal flap 55 of the GEFV 49 (shown in solid lines). As previously mentioned, a principal reason for regurgitation associated with GERD is the mechanical failure of the deteriorated (or reflux appearance) gastroesophageal flap 55 of the GEFV 49 to close and seal against the higher pressure in the stomach. Due to reasons including lifestyle, a Grade I normal gastroesophageal flap 50 of the GEFV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56.

The deteriorated gastroesophageal flap 55 shown in FIG. 2 has a gastroesophageal flap valve 49 and cardiac notch 47 that are both significantly degraded. Dr. Hill and colleagues developed a grading system to describe the appearance of the GEFV and the likelihood that a patient will experience chronic acid reflux. L. D. Hill, et al., *The gastroesophageal flap valve: in vitro and in vivo observations*, Gastrointestinal Endoscopy 1996:44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade III (almost Grade IV) flap valve. A Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently are a device, assembly, and method, which may be employed to advantage according to an embodiment of the invention in restoring the normal gastroesophageal flap valve anatomy.

Figures 3, 4:
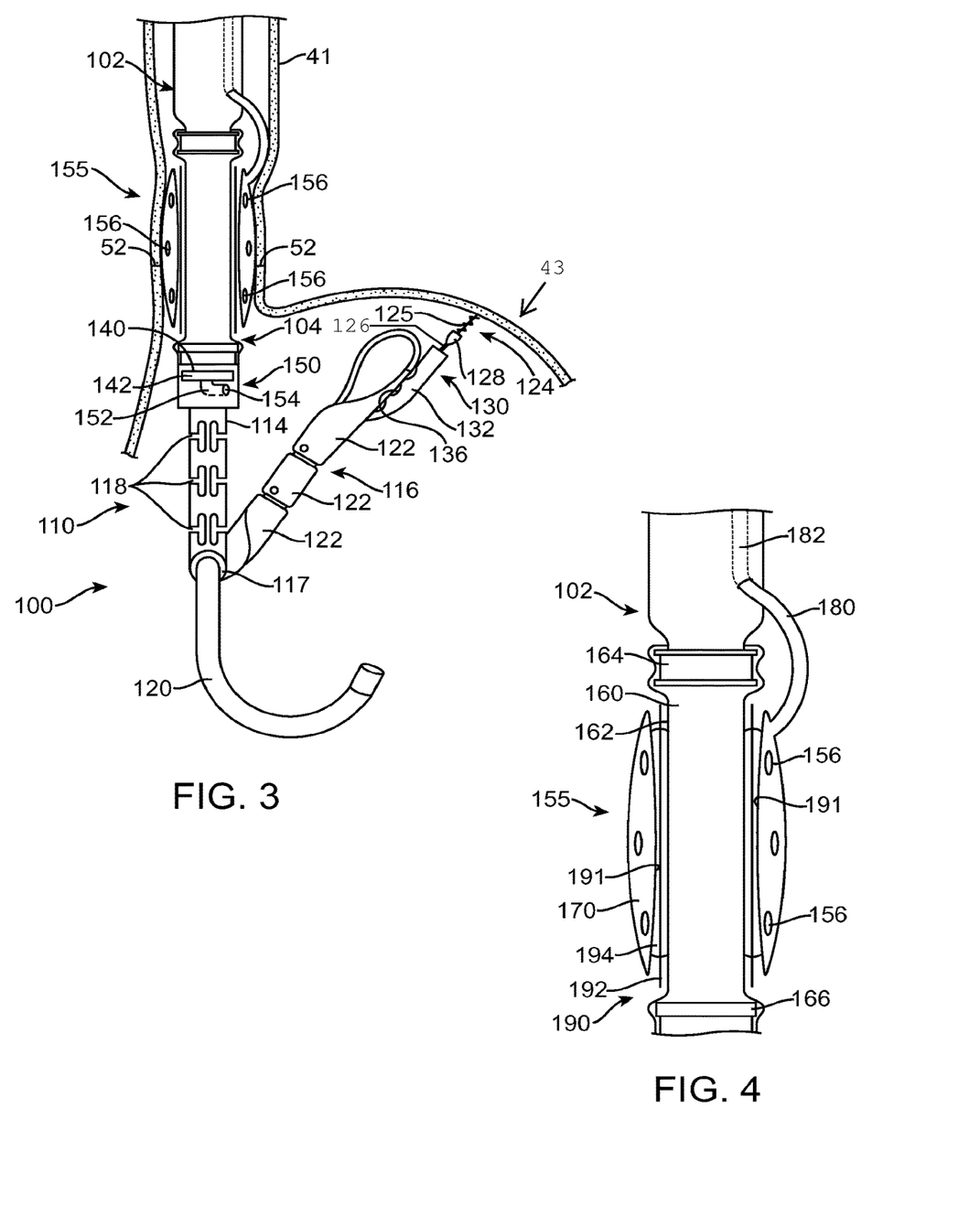
FIG. 3 is a side view of an apparatus for restoring a GEFV having an invaginator according to an embodiment of the invention.
FIG. 4 is a partial side view of the apparatus of FIG. 3 showing the invaginator according to an embodiment of the invention in greater detail.

Referring now to FIG. 3, it shows an apparatus 100 according to an embodiment of the present invention positioned for the restoration of a GEFV. The apparatus 100 includes an elongated member 102 having a distal end 104 for transoral placement into the stomach 43. Carried on the distal end of the elongated member 102 is a device 110 for restoring the GEFV. The device 110 includes a first member 114, hereinafter referred to as the chassis, and a second member 116, hereinafter referred to as the bail. The chassis 114 and bail 116 are hingedly coupled at 117. The chassis 114 and bail 116 form a tissue shaper which, as described in copending U.S. application Ser. No. 11/172,427 and incorporated herein in its entirety by reference, shapes tissue of the stomach 43 into the flap of a restored gastroesophageal flap valve (GEFV).

The device 110 has a longitudinal passage to permit an endoscope 120 to be guided through the device and into the stomach. This permits the endoscope to serve as a guide for guiding the device 110 through the patient's throat, down the esophagus 41, and into the stomach. It also permits the gastroesophageal flap valve restoration procedure to be viewed at each stage of the procedure.

To facilitate shaping of the stomach tissue, the stomach tissue is drawn in between the chassis 114 and the bail 116. Further, to enable a flap of sufficient length to be formed to function as the flap of a gastroesophageal flap valve, the stomach tissue is pulled down so that the fold line is substantially juxtaposed to the opening of the esophagus into the stomach. Hence, the stomach is first gripped at a point out and away from the esophagus and the grip point is pulled to almost the hinged connection 117 of the chassis 114 and bail 116. As described in copending application Ser. No. 11/001,666, filed Nov. 30, 2004, entitled FLEXIBLE TRANSORAL ENDOSCOPIC GASTROESOPHAGEAL FLAP VALVE RESTORATION DEVICE AND METHOD, which application is incorporated herein by reference, the device 110 is fed down the esophagus with the bail 116 substantially in line with the chassis 114. To negotiate the bend of the throat, and as described in the aforementioned referenced application, the chassis 114 and bail 116 are rendered flexible. The chassis 114 is rendered flexible by slots 118 and the bail 116 is rendered flexible by the hingedly coupled links 122. Further details concerning the flexibility of the chassis 114 and the bail 116 may be found in the aforementioned referenced application.

As further shown in FIG. 3, the device further includes a tissue gripper 124. The gripper 124, in this embodiment, comprises a helical coil 125. The coil 125 is carried at the end of a cable 126 and may be attached to the end of the cable or be formed from the cable. In this embodiment, the helical coil 125 is attached to the cable 126 and is preceded by a guide 128 whose function will be described subsequently.

The helical coil 125 is shown in an approximate position to engage the stomach tissue out and away from the opening of the esophagus to the stomach. The helical coil 125 is guided into position by a guide structure 130 carried on the bail 116. The guide structure 130 comprises a guide tube 132. When the device 110 is first introduced down the esophagus into the stomach, the helical coil 125 is caused to reside well within the guide tube 132 to preclude the helical coil from accidentally or inadvertently snagging esophageal or stomach tissue.

The guide tube includes a longitudinal slit 136 having a circuitous configuration. The slit 136 permits the end of the cable to release or disassociate from the bail after the stomach tissue is gripped. The circuitous configuration of the slit 136 assures confinement of the cable 126 within the guide tube 132 until release of the cable is desired. The proximal end of the slit 136 has an enlarged portion or opening (not shown). This opening permits the cable and helical coil to reenter the lumen when the device 110 is readied for a repeated stomach tissue shaping procedure. To that end, the guide 128 has a conical surface that serves to guide the cable end back into the opening of the slit 136.

With continued reference to FIG. 3, the device 110 further comprises a fastener deployer 150. The fastener deployer includes at least one fastener deployment guide 152. The fastener deployment guide 152 takes the form of a guide lumen. Although only one guide lumen 152 is shown, it will be appreciated that the device 110 may include a plurality of such lumens without departing from the invention. The guide lumen terminates at a delivery point 154 where a fastener is driven into the molded stomach tissue. The fastener deployer may take the form of any one of the assemblies fully described and claimed, for example, in copending U.S. application Ser. No. 11/043,903 which application is owned by the assignee of this invention and incorporated herein by reference.

The device 110 further includes a window 140 within the chassis 114. The window is formed of a transparent or semi-transparent material. This permits gastroesophageal anatomy, and more importantly the gastroesophageal junction 52 (Z-line) to be viewed with the endoscope 120. The window includes a location marker 142 which has a known position relative to the fastener delivery point 154. Hence, by aligning the marker with a known anatomical structure, the fastener will be delivered a known distance from or at a location having a predetermined relation to the marker. For example, by aligning the marker with or below the Z-line, it will be known that the fastener will be placed aboral of the Z-line and that serosa tissue will be fastened to serosa tissue. As previously mentioned, this has many attendant benefits.

According to this embodiment, the apparatus 100 further includes invaginator 155. The invaginator 155 is a double walled toroidal structure 170 having a hollow center. A plurality of orifices 156 communicate with the hollow center. These orifices 156, are used to pull a vacuum to cause the invaginator 155 to grip the tissue wall of the esophagus. This will serve to stabilize the esophagus and maintain device 110 positioning during the procedure. This vacuum gripping of the esophagus may also be used to particular advantage if the patient suffers from a hiatal hernia.

More specifically, the invaginator 155 is so arranged with respect to the elongated member 102 that, once the invaginator grips the esophagus 41, the device is permitted very little axial movement with respect to the invaginator but is permitted relatively free rotational movement with respect to the invaginator. This permits the device 110 to be rotated in increments for stomach tissue folding while maintaining a substantially constant axial position within the stomach. Hence, the invaginator 155 avoids the prior need of releasing the invaginator to permit device rotation and then realigning the device at the proper axial position for the next incremental folding procedure.

As may be best noted in FIG. 4, the invaginator 155 is seated against a bearing surface portion 160 of the elongated member 102. The bearing surface portion 160 is formed from a tubular member 162 which is secured in place by retention rings 164 and 166. The toroidal or ring structure 170 circumscribes the bearing surface portion and is axially confined between retention rings 164 and 166. The interior of the ring structure 170 may be coupled to a vacuum source (not shown) through a flexible conduit 180 and a lumen 182 in the elongated member 102. This permits the invaginator to non-invasively grip the esophagus through a vacuum-grip applied through orifices 156. The conduit 180 may be covered by a thin membrane or sheath (not shown) to help prevent the conduit 180 from snagging during deployment.

The bearing surface portion 160 forms part of a bearing assembly 190 coupling the invaginator 155 to the elongated member 102. The bearing assembly further includes an inner bearing surface 191 of the ring structure 170. This bearing assembly 190 permits relatively free relative rotational movement of the elongated member 102 and thus device 110 with respect to the invaginator 155 and the anatomy.

The bearing assembly 190 may further include an optional bearing sleeve 192 between the inner bearing surface 191 and bearing surface portion 160 and axially between the retention rings 164 and 166. The sleeve 192 serves to further reduce friction against the spaces between the sleeve 192 and surface portion 160 and surface 191 may be packed with a suitable lubricant 194 to still further reduce rotational friction.

In use, as described in the aforementioned copending U.S. application Ser. No. 11/172,427, the device 110 is introduced through the patient's mouth, throat, esophagus and into the stomach with the bail 116 substantially in line with the chassis 114. After the z line is observed through the window 140 and the marker 142 set at or aboral of the z line, the stomach 43 is partially inflated to permit visualization with the endoscope 120. This allows a first gripping site within the stomach for the first fold to restore the GEFV. When the site is found, a vacuum is pulled through the invaginator 155 to grip the esophagus. The helix 125 is then screwed into the stomach wall. The stomach is then pulled between the chassis 114 and the bail 116 to form a first fold and one or more fasteners are delivered by the fastener deployer 150 to maintain the first fold. Then, the helix 125 is released from the stomach tissue.

At this point in the prior art, it has been necessary to release the invaginator vacuum grip to permit the assembly 100 to be rotated for the next incremental fold. The position of the device 110 would then be checked by moving the endoscope 120 back for visualizing the device and the z line would be located through the window 140. The axial position of the device would then be adjusted if necessary. The vacuum grip would then be reestablished by the invaginator for the next incremental fold.

In contrast, by virtue of the invaginator of this embodiment, the vacuum grip need not be interrupted to permit rotation of the device 110 in the proper position for the next incremental fold. Once the helix 125 releases the tissue, the device may be rotated with the bearing assembly 190. The next fold may then be made. No other repositioning of the device or manipulation of the endoscope is necessary.

To further assist maintaining the invaginator 155 in its axial position on elongated member 102, or as a sole means along with conduit 180, the invaginator 155 may be tethered to the chassis 114 by a flexible non-stretchable tether (not shown). This may serve to eliminate the need for retention rings 164 and 166.

Figures 5, 6:
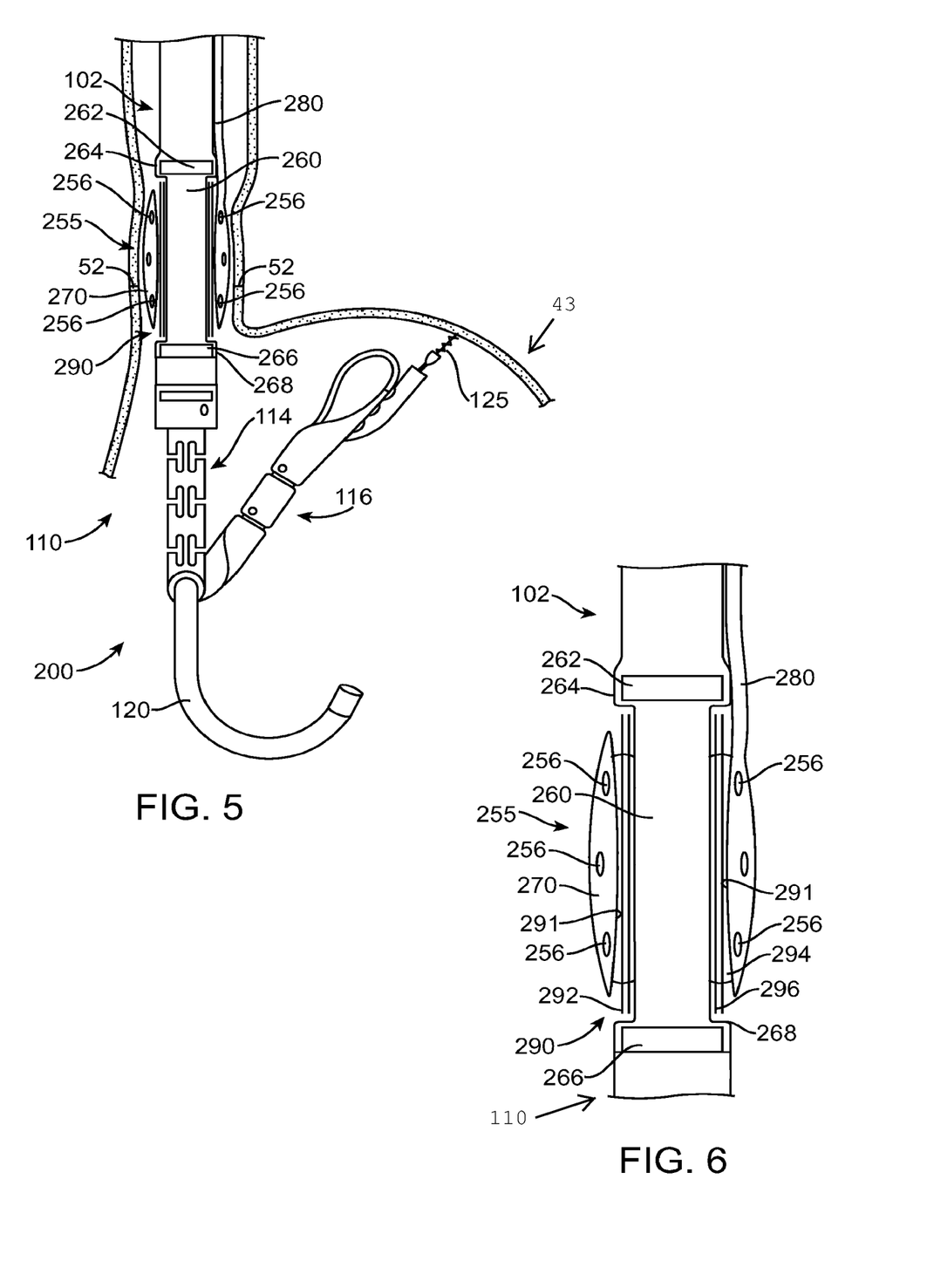
FIG. 5 is a side view of another apparatus for restoring a GEFV including an invaginator according to another embodiment of the invention.
FIG. 6 is a partial side view of the apparatus of FIG. 5 showing the invaginator in greater detail.

FIG. 5 shows another assembly 200 according to another embodiment of the present invention. The assembly 200 is essentially identical to the assembly 100 of FIG. 3 except for the design of the bearing surface portion 260, the invaginator 255, and the bearing assembly 290. Hence for clarity, like reference numerals for like elements have been carried over from FIG. 3 to FIG. 5.

FIG. 6 shows the bearing surface portion 260 and bearing assembly 290 in greater detail. As may be noted, the bearing surface portion 260 is an extension of the elongated member 102 and is partly defined by a ring 262 which creates an annular retention shoulder 264. The other end of the bearing surface portion 260 is sealed to another ring 266 carried by the device 110 to form another retention shoulder 268. Again, the invaginator 255 includes a hollow double walled ring 270 that circumscribes the bearing surface portion 260. The invaginator ring 255 includes orifices 256 through which a vacuum may be drawn for vacuum gripping the esophagus. The vacuum is pulled through a conduit 280 that extends along side and external to the elongated member 102.

The bearing assembly 290, according to this embodiment, includes a pair of bearing sleeves, an outer bearing sleeve 292 and an inner bearing sleeve 296. The bearing sleeves 292 and 296 are coaxially arranged about the bearing surface portion 260. Again, a suitable lubricant 296 may be provided between the inner bearing surface 291 of ring 270 and sleeve 292, between sleeve 292 and sleeve 296, and between sleeve 296 and the bearing surface portion 260.

Each of the invaginators described herein may be rendered flexible by being formed of flexible material. This enables the invaginators to conform to non-circular structures while still permitting rotation.

The assembly 200 may be used as previously described with respect to assembly 100. The conduit 280 is preferably flexible to permit relatively free rotational movement of the elongated member 102 and device 110 with respect to the invaginator ring 270 and hence the anatomy.

Figure 7:
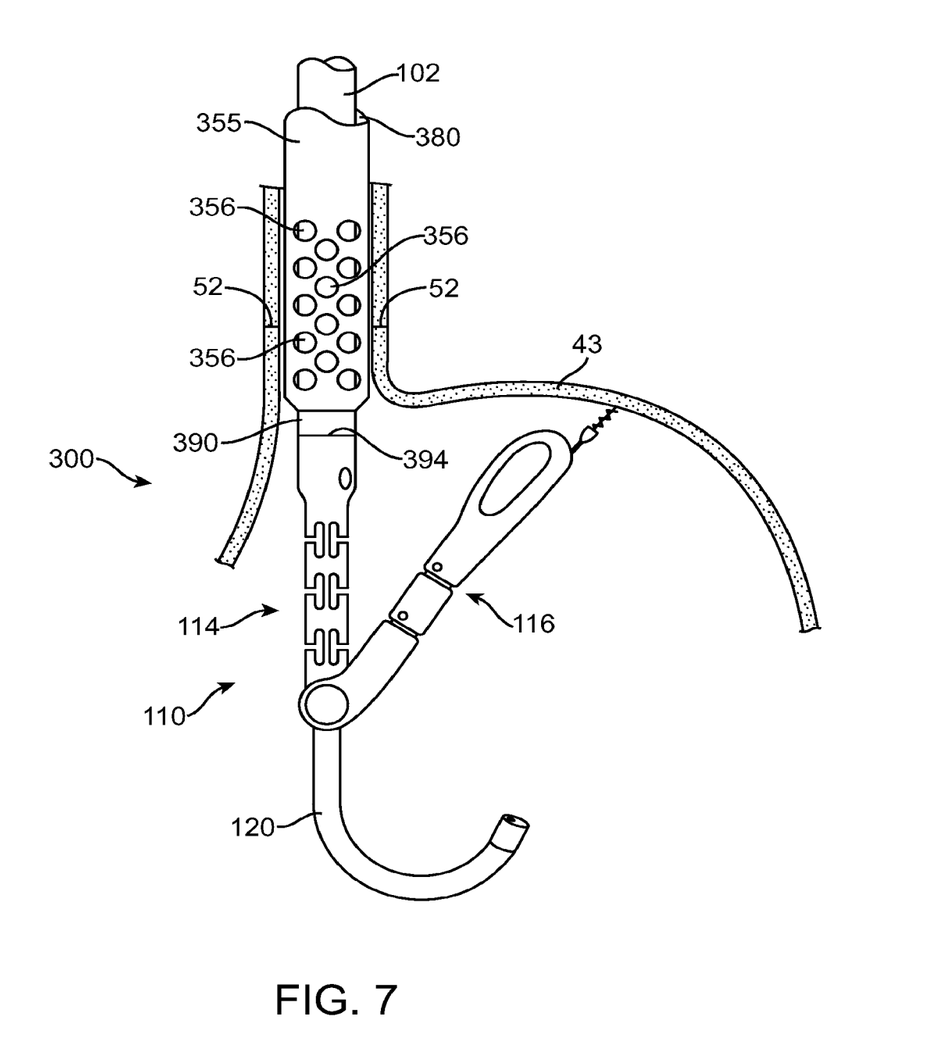
FIG. 7 is a side view of an apparatus according to a still further embodiment.

FIG. 7 shows another assembly 300 according to still another embodiment of the present invention. The assembly 300 is again essentially identical to the assembly 100 of FIG. 3 in terms of the device 110 but differs in the design of the invaginator 355. Again, for clarity, like reference numerals for like elements have been carried over from FIG. 3 to FIG. 7.

As may be noted in FIG. 7, the invaginator 355 is full length in that it may extend orally along the length of and substantially coextensive with the elongated member 102. The invaginator 355 still includes orifices 356 through which a vacuum may be drawn for vacuum gripping the esophagus. The vacuum may be pulled through a conduit (not shown) or the annular space 380 between the elongated member 102 and the invaginator 355.

According to this embodiment, the invaginator includes a sealed bearing 390 permitting the elongated member 102 and device 110 to freely rotate with respect to the invaginator 355. A suitable lubricant may be provided between the bearing 390 and the device 110 at the adjoining surfaces 394.

The assembly 300 may be used as previously described with respect to assembly 100. The conduit invaginator 355 is preferably flexible to permit the assembly to be fed through the throat, and esophagus into the stomach 43.

While particular embodiments of the present invention have been shown and described, modifications may be made, and it is thereto intended in the appended claims to cover all such changes and modifications which fall within the true spirit and scope of the invention.

What is claimed is:

1. A method of restoring a flap of a deteriorated Grade III or Grade IV gastroesophageal flap valve associated with a stomach and esophagus, comprising:
   providing an elongated member having a tissue shaper at a distal end thereof;
   inflating the stomach;
   gripping a tissue wall of the esophagus using an invaginator having a plurality of orifices to pull a vacuum;
   gripping stomach tissue with the tissue shaper from within the stomach aboral of a Z-line;
   pulling the gripped stomach tissue into a mold to form a first fold of stomach tissue;
   pulling the stomach downwardly to align a fold line in the first fold of stomach tissue aboral of the Z-line;
   deploying a first fastener through the first fold of stomach tissue aboral of the Z-line; and rotating the elongated member while maintaining an axial position of the invaginator relative to the esophageal wall in order to form a sequential, second fold of stomach tis sue.

2. The method of claim 1, wherein the first fastener extends through the first fold of stomach aboral of the Z-line so that serosa tissue is fastened to serosa tissue.

3. The method of claim 1, further comprising deflating the stomach after deploying the first fastener.

4. The method of claim 1, further comprising releasing the grip on the stomach tissue after the first fastener is deployed.

5. The method of claim 1, further comprising maintaining the gripping of the tissue wall of the esophagus and repeating the inflating, gripping of stomach tissue, pulling, deploying, and rotating steps for forming the second fold of stomach tissue and deploying a second fastener displaced from the first fastener.

6. The method of claim 1, wherein the inflating step includes inflating the stomach to a first pressure, wherein the method further comprises visualizing the stomach from within the stomach after inflating the stomach to the first pressure, and increasing inflation pressure within the stomach to a second pressure after visualizing the stomach before gripping stomach tissue.

* * * * *